United States Patent [19]

Larsonneur

[11] Patent Number: 4,701,156
[45] Date of Patent: Oct. 20, 1987

[54] METHOD AND APPARATUS FOR FABRICATING THREE-FOLD PADS

[75] Inventor: Lionel M. Larsonneur, Pomona, Calif.

[73] Assignee: Paper-Pak Products, Inc., La Verne, Calif.

[21] Appl. No.: 842,546

[22] Filed: Mar. 21, 1986

Related U.S. Application Data

[63] Continuation of Ser. No. 427,165, Sep. 29, 1982, abandoned.

[51] Int. Cl.$^4$ .............................................. B31F 1/00
[52] U.S. Cl. ................................... 493/418; 493/423; 493/438; 493/455
[58] Field of Search .................. 53/117, 429; 206/440, 206/441, 494; 604/289, 358, 385 R, 385.1, 389; 493/418, 423, 438, 441, 450, 455, 458, 938, 967

[56] References Cited

U.S. PATENT DOCUMENTS

| | | | |
|---|---|---|---|
| 1,673,763 | 6/1928 | Flather | 206/494 |
| 3,369,544 | 2/1968 | Crockford | 604/385.1 X |
| 3,502,322 | 3/1970 | Cran | 493/418 X |
| 3,635,462 | 1/1972 | Joa | 493/438 X |
| 3,963,029 | 6/1976 | Brooks | 604/289 |
| 4,022,457 | 5/1977 | Marin et al. | 493/423 X |

Primary Examiner—Robert L. Spruill
Assistant Examiner—Steven P. Weihrouch
Attorney, Agent, or Firm—Henry M. Bissell

[57] ABSTRACT

Apparatus and methods of operation for automatically folding obstetrical pads into a so-called three-fold configuration which occupies approximately 40% less volume than two-fold pads of the prior art. The obstetrical pads, as fabricated, have two opposed, elongated tab portions extending beyond the pad proper, and the pad is folded by the apparatus so that these tab portions are juxtaposed adjacent one another in order to facilitate removal of the pad from its package and provide enhanced convenience in preparation of the pad for use. More importantly, the placement of the tab portions in this fashion permits the handling of the pad without contaminating the sterile field in the inner fold area of the pad. By virtue of the reduced volume of the three-fold pad, substantial savings are realized in the manufacturing process, in the storage facilities required for warehousing and inventory at each step in the distribution process, as well as in shipping. The folding apparatus comprises a plurality of stations located in sequence to which each pad is directed in succession by a series of operationally synchronized conveyor belts and drive cylinders, wherein separate steps in guiding the respective folding and positioning operations are performed. Selectively directed blasts of air at strategic points in the folding apparatus are used to assist in the folding and positioning steps.

19 Claims, 17 Drawing Figures

METHOD AND APPARATUS FOR FABRICATING THREE-FOLD PADS

This is a continuation of application Ser. No. 427,165, filed Sept. 29, 1982, now abandoned.

BACKGROUND OF THE INVENTION

1. Field of the Invention

This invention relates to methods and apparatus for folding absorbent pads of the type used with obstetrical patients under post-natal care and, more particularly, for folding the pads by thirds in order to achieve more compact packaging of the pads.

2. Description of the Prior Art

Various products have been designed for absorbing excreted body fluids, for example feminime hygiene products. One such type of product, the tampon, is clearly unsuitable for obstetrical patients. Obstetrical pads are more similar to sanitary napkins, but have been particularly designed for use with an obstetrical patient within the first few days after delivery. Obstetrical pads are substantially larger and contain more absorbent material in order to perform satisfactorily in absorbing and containing the moisture encountered in use.

Obstetrical pads, as they have been developed, commonly comprise two highly absorbent fluff pads with layers of soft cellulose tissue in between and fully enclosing them. The natural wicking action of the tissue draws the moisture from the center out to the ends of the pad. This complete, even dispersion allows the fluff pads to absorb their maximum capacity. The collected moisture is then contained within a soft polypropylene shielf to prevent soiling of clothes or linen. The outside enclosing layer, a non-woven covering of substantially tubular form, extends in both directions past the ends of the inner fluff pads and tissue layers to provide a pair of high-tensile tabs, or "tails", to provide the means by which the pad is held in proper position in use.

Until recently, obstetrical pads of this type have been folded in half and packed in individual oblong packages. This manner of folding places the contact portion of the pad inside, thus maintaining a sterile field in this region. Folding in this manner also naturally, places both of the end tabs or "tails" together at the same end of the package, thus making them readily available to the nurse or other personnel opening the package to grasp the tails and use them as handles in placing the pad in position for use. This provides a professional advantage in that the medical practitioner can easily handle the pad without contaminating the sterile field.

Recently, however, it has been discovered that substantial savings in packing space can be realized from the folding of the pads in thirds, thus developing so-called "three-fold" pads. The resulting package of a single pad is more cubical in form than the oblong packs containing the "two-fold" pads. It has been found that three-fold pads can be packaged in as much as 40% less volume than a comparable number of two-fold pads, the improvement in packing space being derived principally from the greater compressibility of the fluff layers when the pads are folded in thirds. This greater compactness of the three-fold pads results in substantial savings in processing and storage at various points along the line from the manufacturing plant to the inventory storage of the ultimate user. For example, after the pads are manufactured, folded and individually packaged, they are placed in bags of one dozen each and the bags are placed in shipping cartons. These cartons are run through a sterilizer in which the air is first evacuated and then steam at approximately 200° F. is introduced to permeate through the package wrappings and sterilize the contents. Because of the substantial reduction in the volume of the individual pads, the grade of throughput in the sterilizer is substantially increased. Less warehouse space is required for the storage of a given number of pads. Because the pads are extremely light for their volume, so that the limitation on transport is volume rather than weight, a given truck or other transport vehicle can carry a substantially greater number of pads. The inventory storage capacity at the hospital or other customer is correspondingly improved, again resulting in savings derived from the increased compactness of the pads.

A further benefit is realized from the development of the three-fold pad. With two-fold pads, the single fold thereof is in the middle, the point at which a crease develops the most discomfort for the user. With the three-fold pad, the folds are displaced from the center of the pad and one of the folds, being folded about another portion of the pad, does not present a crease at all. However, in the folding of the pad in thirds, unlike the folding of a pad in half, the two end portions or tails do not naturally end up adjacent each other and particular pains must be taken in the folding of the three-fold pad in order to achieve this convenience for the user of placing the tails together for ready access when the package is opened and, more importantly, the capability of handling the pad without contaminating the sterile field. Because of the problems involved in the folding of the three-fold pads, particular methods and apparatus have been developed to achieve the desired folding as the manufactured pads come off the fabrication production line.

SUMMARY OF THE INVENTION

In brief, arrangements in accordance with the present invention comprise pad folding apparatus wherein an unfolded pad is folded twice and compressed to provide a compact pad which requires up to 40% less storage space than currently packaged pads. The apparatus receives the unfolded pad with the leading tail protion folded under the pad and the trailing tail being free to hang substantially vertically. Drive means cause the pad to advance within the apparatus and at a certain point during advancement the front portion of the pad is caused to hang substantially vertically adjacent a rounded portion of a support member. Further advancement of the pad causes the vertically extending portion of the pad to be directed at an angled member and toward the rear portion of the pad. The angled portion of the pad is then compressed between a pair of belts and continued movement of the pad causes the angled portion of the pad to be positioned in a substantially horizontal direction toward the rear portion of the pad. Continued movement of the pad causes the rear portion of the pad to be unsupported and forced against an angled member such that the rear portion of the pad is folded in a direction towards the front portion of the pad. At this time, the pad is again compressed. Further advancement of the pad brings the pad into engagement with a support member such that the second fold is substantially smooth. Continued movement of the pad causes the rear portion of the pad to be extended in the direction towards the front portion of the pad with the rear tail portion extending out towards the front portion of the pad. Continued movement of the pad causes this tail portion to be folded and extend towards the rear portion of the pad into juxtaposition with the other tail portion. Compression means are then applied to the bottom and top of the pad to compress the three folded layers into the final form of the pad for insertion into an individual package.

BRIEF DESCRIPTION OF THE DRAWING

A better understanding of the present invention may be had from a consideration of the following detailed description, taken in conjunction with the accompanying drawings in which.

DESCRIPTION OF THE PREFERRED EMBODIMENT

Figure 1:
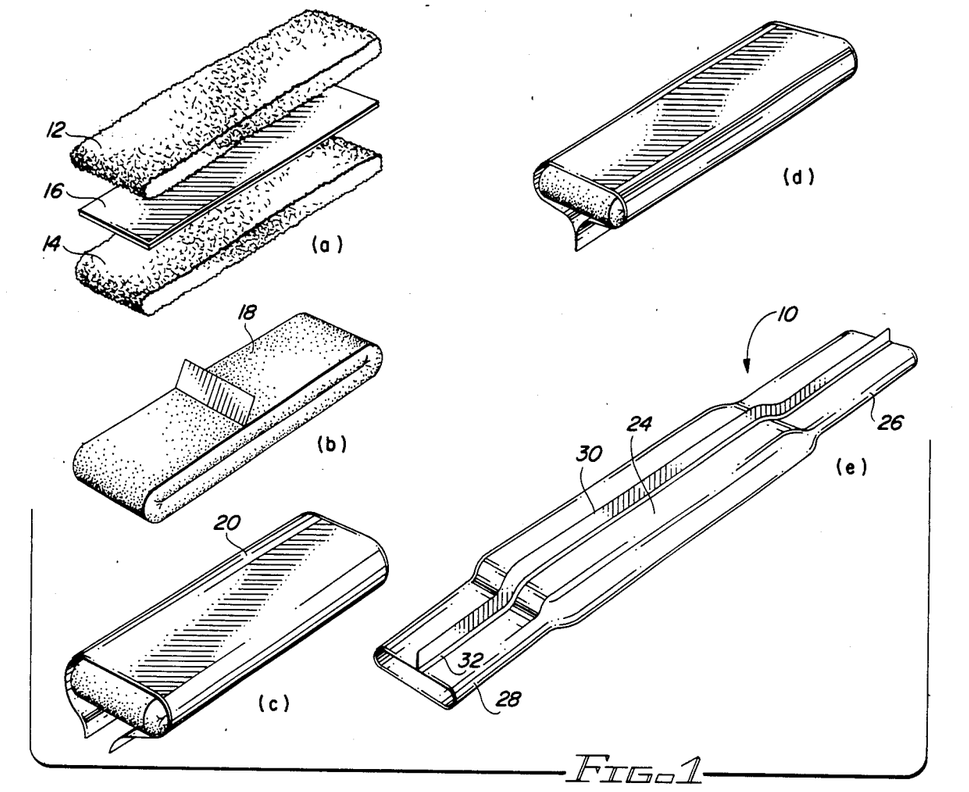
FIG. 1 shows the component parts of an obstetrical pad of the type involved herein.

FIG. 1 shows in an exploded view the construction of an obstetrical pad 10 to be folded in accordance with the teachings of the present invention. The innermost part of pad 10, shown in FIG. 1(a), comprises two layers 12 and 14 made of fluff material, such as 100% virgin pulp for maximum absorbency. Center tissue 16 is provided for mid-pad dispersion. FIG. 1(b) shows the structure of FIG. 1(a) sandwiched between an outer wrap layer of soft cellulose tissue 18. Tissue 18 is cut so that its grain runs lengthwise along pad 10, its natural wicking action drawing the moisture out to the ends of the pad 10. FIG. 1(c) shows the structure of FIG. 1(b) wrapped in a plastic (preferably soft polypropylene) film 20 to contain the collected moisture to prevent soiling of clothes or linen. FIG. 1(d) illustrates the addition of a second layer tissue 22 for additional dispersion of collected moisture. FIG. 1(e) shows the structure of FIG. 1(d) covered with a smooth, soft, unwoven material 24 for the outer wrap of the pad 10 and includes two opposed tail portions 26 and 28. The overlap 30 of the material 24 can be sealed to the underlying tissue material by using a melt material. Preferably, this melt material is in color, such as blue, to clearly show the proper side to wear away from the body.

Figure 2:
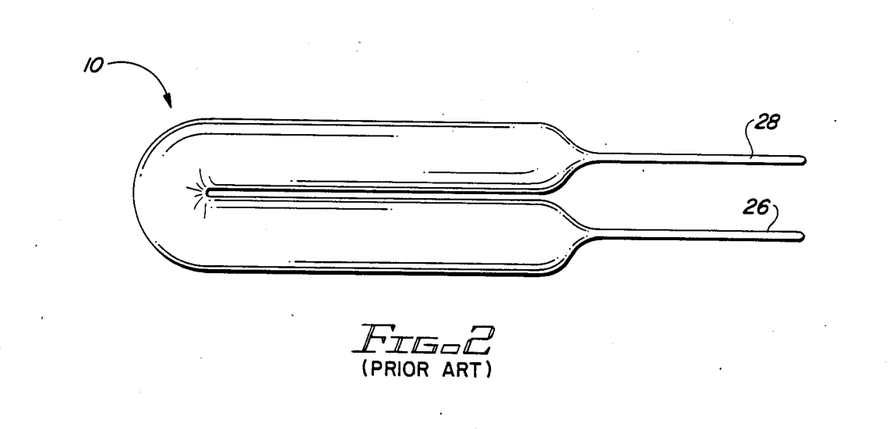
FIG. 2 shows a pad folded in accordance with prior art techniques.

FIG. 2 shows the pad of the type shown in FIG. 1 as typically folded in the prior art; i.e., a single-fold, double layer pad is provided with tails 26 and 28 extended in the manner shown. The length of pad 10, including tails 26 and 28, is on the order of 20 inches; the thickness of the pad at the central area is on the order of ½ inch; and the width of the pad is on the order of three inches.

Figure 3A:
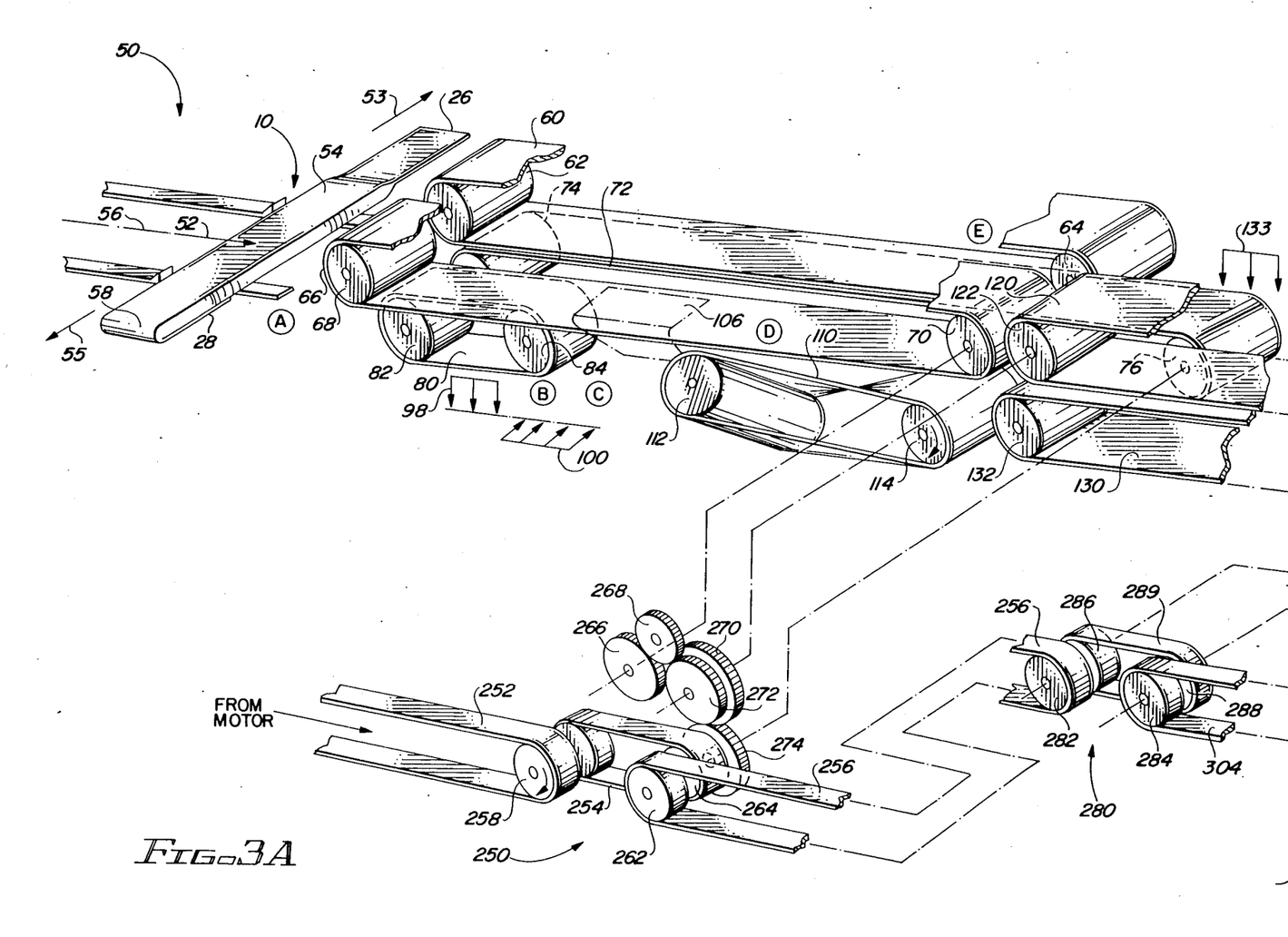
FIG. 3 is shown in two sections, FIGS. 3A and FIG. 3B, as an exploded, simplified view of folding apparatus in accordance with the teachings of the present invention.
Figure 3B:
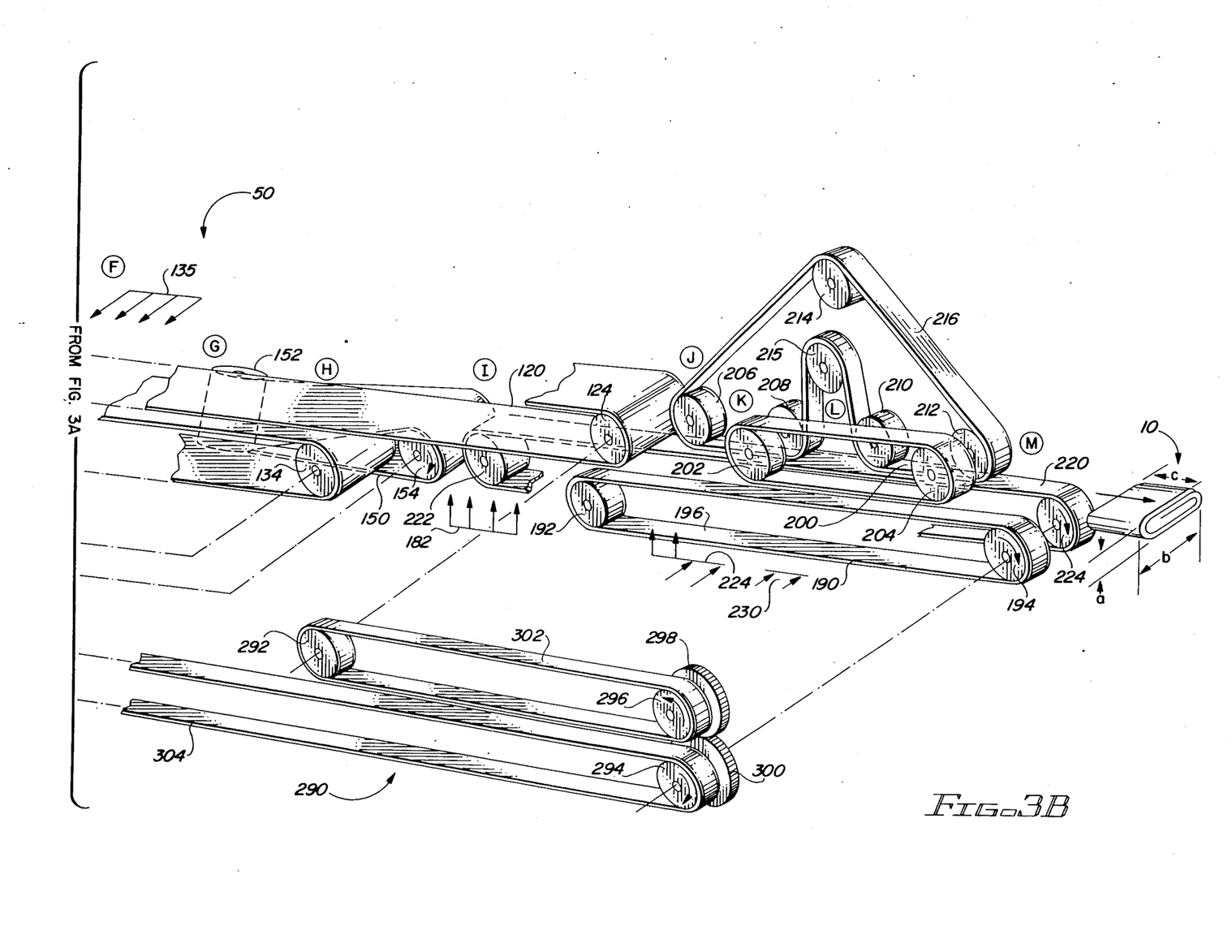

FIG. 3 shows, in simplified form, the apparatus 50 of the present invention which can be utilized to fold and compress a fabricated pad 10 in a manner such that the packaging volume for the pad has been substantially reduced. FIGS. 4(a)–4(m) illustrate the various operations performed on pad 10 as it is driven from the input station of apparatus 50 to the output station.

As shown in these figures, a pad 10 is introduced to the apparatus 50 in a manner such that tail 28 is initially folded under the body of pad 10 and tail 26 is extended horizontally as shown. As will be described in more detail hereinafter, pad 10 will move through the apparatus 50 in the direction of arrow 52. It will be convenient for the purposes described herein to designate various portions of pad 10 in a manner such that the operation of apparatus 50 can be more clearly explained. In this regard, tail 26 will be referred to hereinafter as the rear tail portion; tail 28 will be referred to as the front tail portion; and the body, or flow receiving portion, of pad 10 will be divided into two portions: rear portion 54 on one side of the transverse centerline 56 and front pad portion 58 on the other side of the centerline 56. Further with respect to the directions, if a portion of pad 10 is referred to as extending in the rear direction, it is in the direction of arrow 53, and if referred to as extending in the front direction, it is in the direction of arrow 55.

Figure 4A:
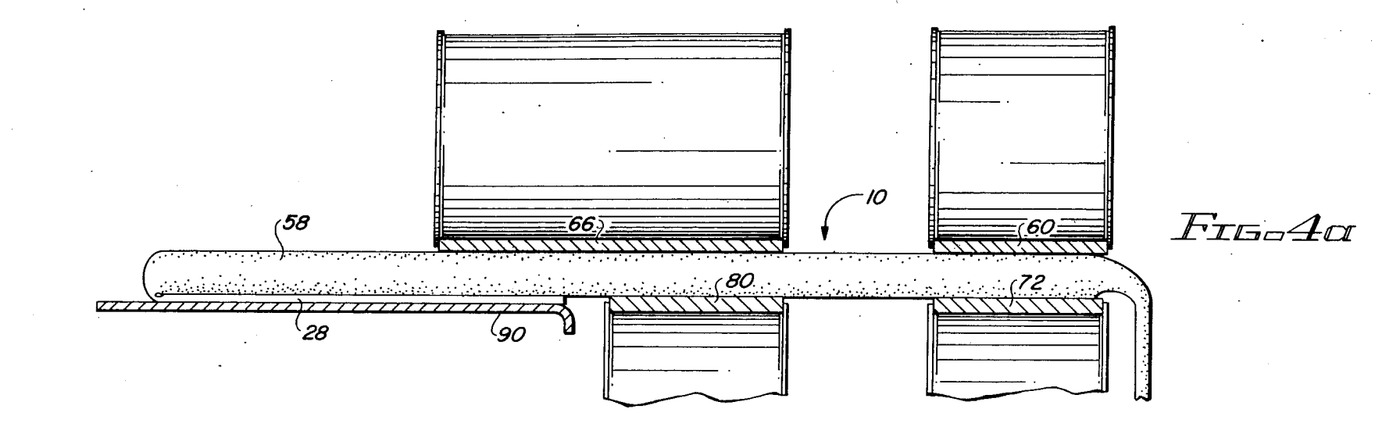
FIGS. 4(a) to 4(m) show, in a series of simplified sectional end views, the steps performed on the pad as it moves through the folding apparatus shown in FIG. 3 and, in the final views, the form of the three-fold pad.
Figure 4B:
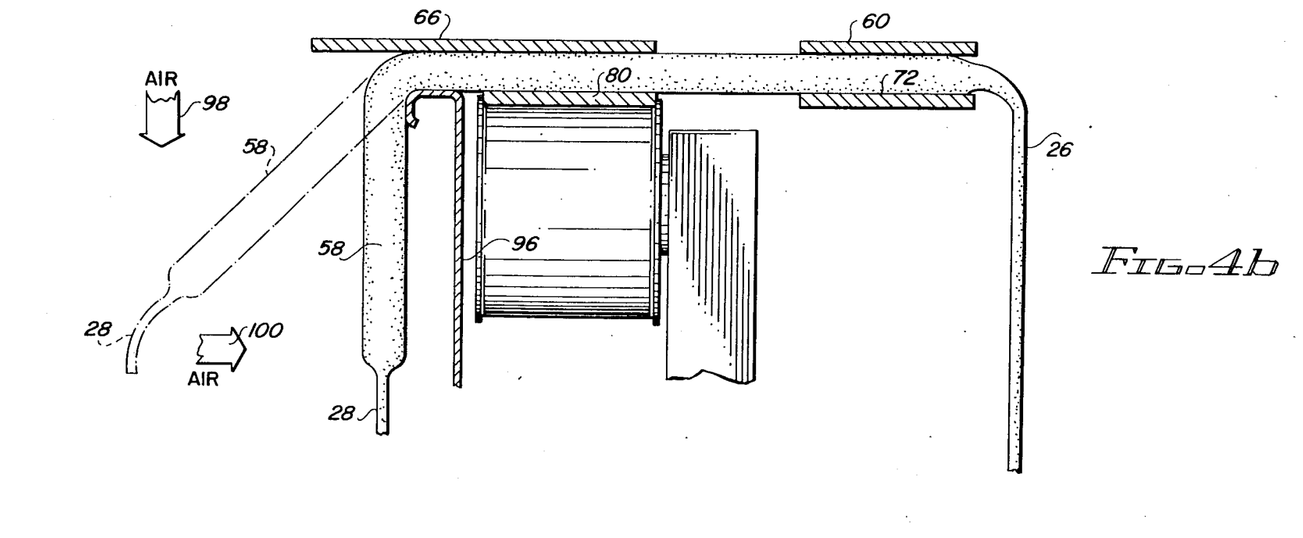
Figure 4C:
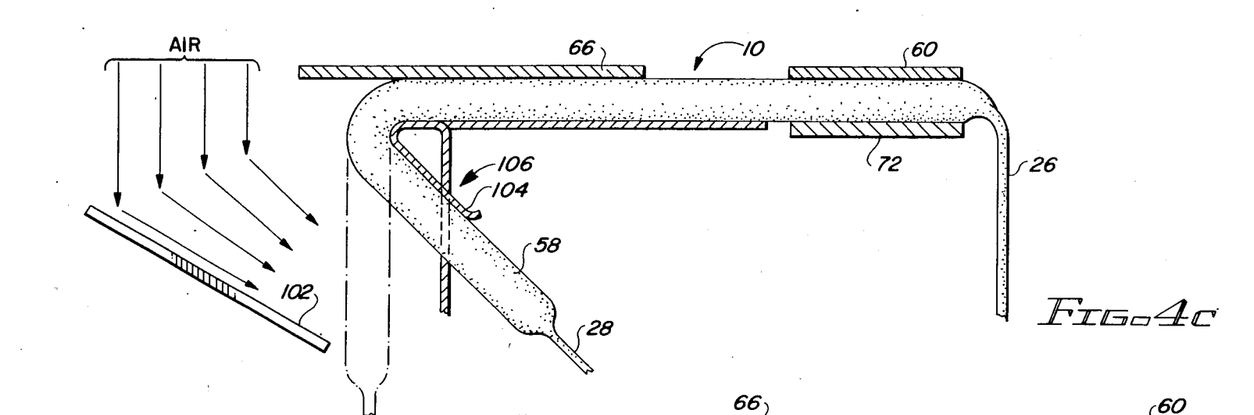
Figure 4D:
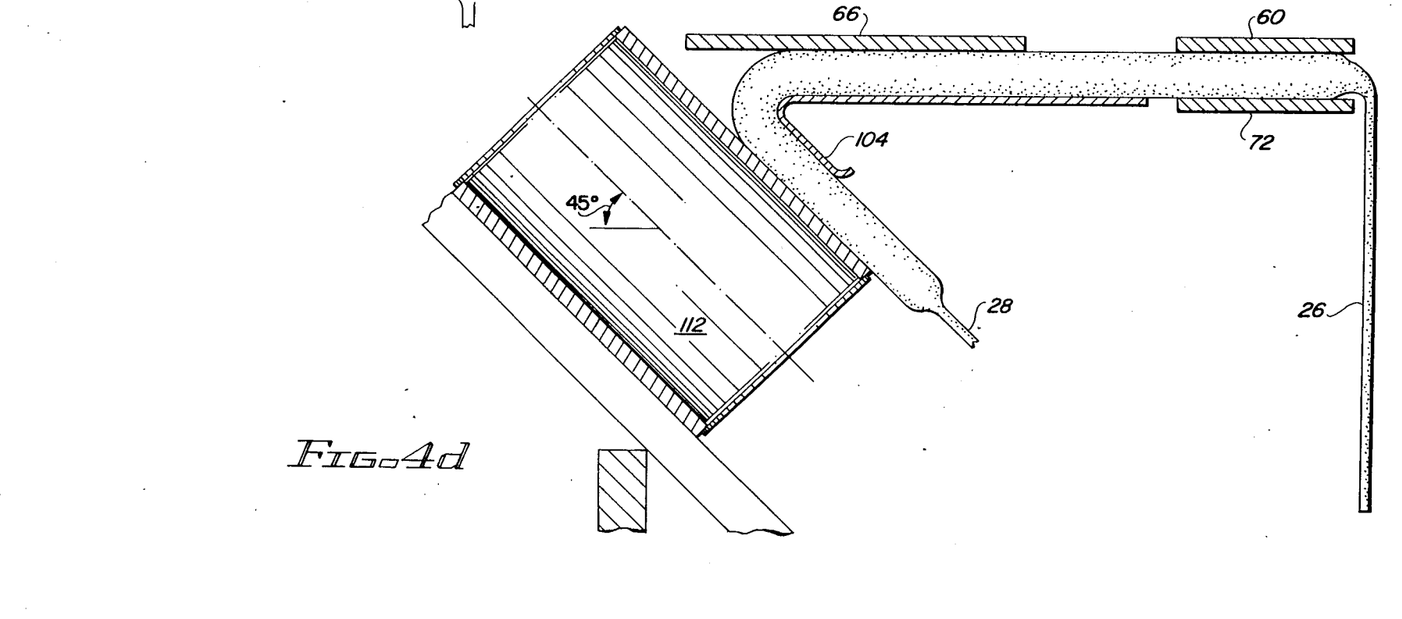

Pad 10 is initially directed to the series of drive belts and drive cylinders as now described. These drive belts are of the cog belt type, sometimes referred to as timing belts, and the pulley surfaces are shaped to matingly engage the cog belts so that the various folding operations can be driven in synchronism. Drive belt 60 is formed about drive cylinders 62 and 64; drive belt 66 is formed about drive cylinders 68 and 70; drive belt 72 is formed about drive cylinders 74 and 76 and drive belt 80 is formed about drive cylinders 82 and 84. The status of the pad 10 at position A is shown in FIG. 4(a) and illustrates that the four drive belts 60, 66, 72 and 80 engage the pad 10 as shown. It is also to be noted that the front pad portion 58 is supported on a support plate 90. As the belts are driven, in the manner to be described hereinafter, pad 10 advances to a position illustrated by reference letter B which corresponds to the partial sectional end view shown in FIG. 4(b). At this position, or station, the support plate 90 has been removed from the process path and replaced by an angled member 92 having a rounded corner portion 94 and a vertical extension 96. In sequence, two blasts of directional air are applied against the front pad portion 58. In particular, a blast of air, represented by reference numeral 98, is applied in a downward direction to portion 58 and thereafter a blast of air, represented by numeral 100, is applied in a horizontal direction to move the pad portion 58 from the position illustrated in phantom to the position illustrated in solid lines. After this operation, pad 10 is advanced to the next operating station indicated by reference letter C which corresponds to the partial sectional side view shown in FIG. 4(c). At this position, a blast of air is deflected by an air deflector/guide member 102 and directs the portion 58 of pad 10 against leg 104 of an angled member 106. Leg 104 extends at an angle toward the direction of arrow 53 as shown. Subsequent to this operation, the pad is advanced to a location indicated by reference letter D, corresponding to the partial sectional view shown in FIG. 4(d). In this portion of the process, an additional drive belt and drive cylinders are utilized. In particular, drive belt 110 is formed about drive cylinders 112 and 114 as shown, the axis of drive cylinder 112 being at an angle of approximately 45° from the horizontal. At this point in the process, belt 110 guides the front portion 58 of pad 10 against the leg 104 of angled member 106, completing the folding begun by the air blast 100.

Figure 4E:
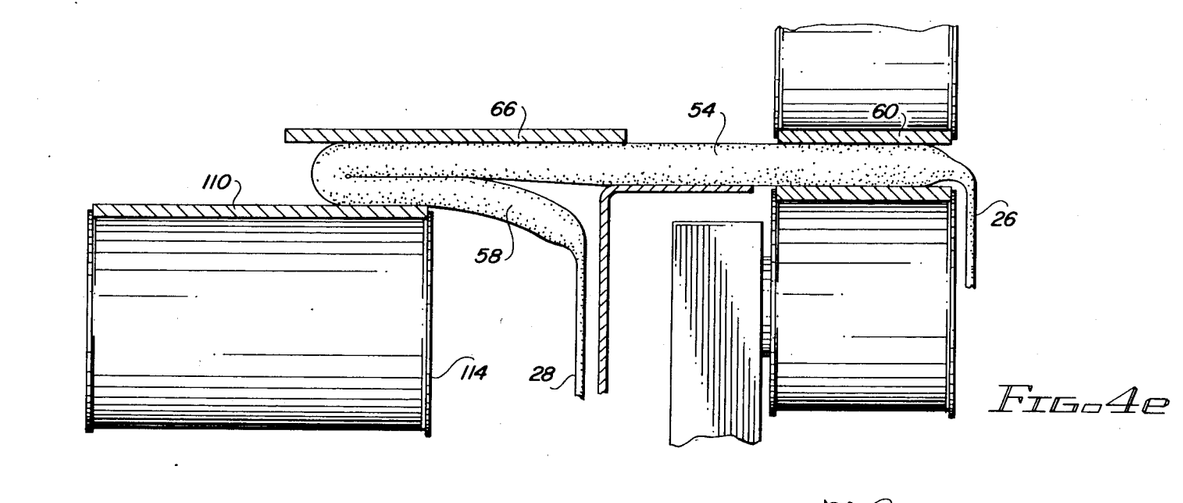

The pad 10 is then advanced to the next station, indicated by reference letter E, wherein additional operations are performed as shown in FIG. 4(e). In particular, drive cylinder 114 with the belt 110 thereon forces pad front portion 58, which is now extending in the direction of arrow 53, into contact with the pad rear portion 54 as shown. At this point, front tail 28 is hanging substantially vertically.

Figure 4F:
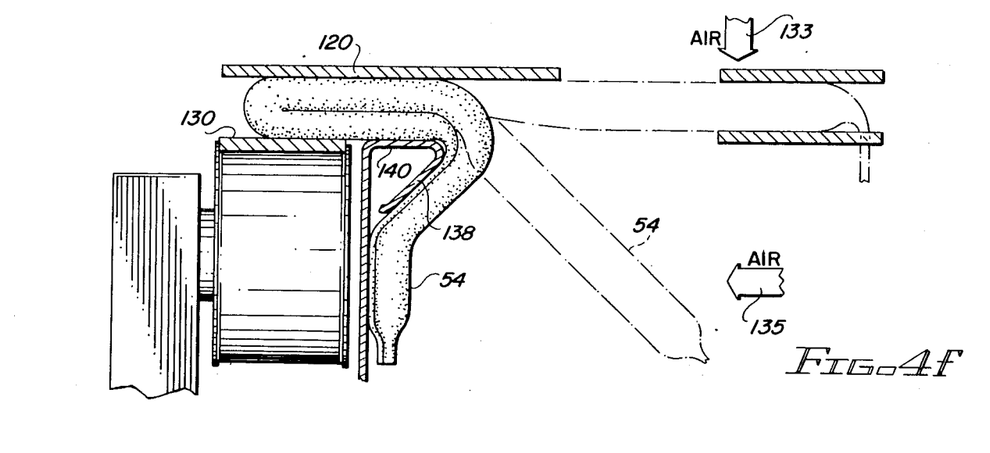

Pad 10 is now advanced to the next station, indicated by reference letter F, shown in more detail in FIG. 4(f). Adjacent this position are two additional drive belts, drive belt 120 supported around drive cylinders 122 and 124 and drive belt 130, supported about drive cylinders 132 and 134. At this point in the process, the pad has progressed out from under drive belt 60, thereby allowing rear pad portion 54 to be subject to a directing, or positioning force. In particular, a blast of air, represented by arrow 133, is first applied to pad rear portion 54. Sequentially thereafter, a horizontal blast of air, represented by arrow 135, is applied to rear pad portion 54 and forces that portion against angled arm 138 at angled support member 140, thereby forcing rear pad portion 54 from the position shown in phantom to the position shown in solid lines in FIG. 4(f). Thus, at this point in the process, the second fold (third layer) has been initiated. It should be noted that any suitable means can be utilized to generate the blasts of air, including commercially available air blowers, and thus this apparatus has not been described in detail.

Figure 4G:
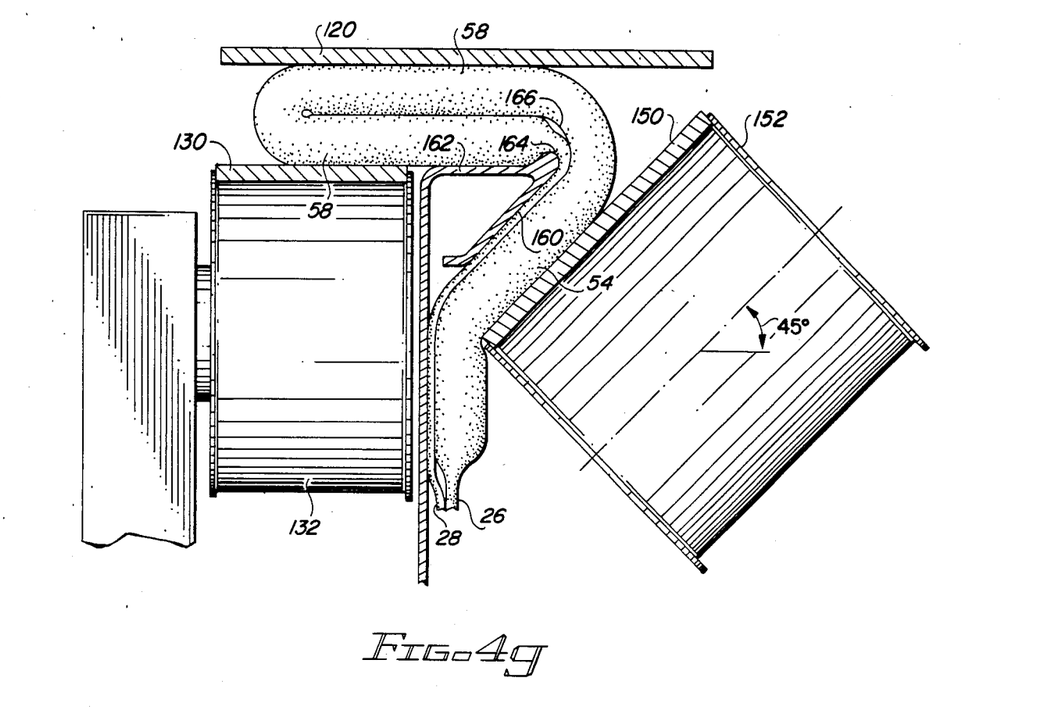

When this operation has been completed, pad 10 moves to the next station G, shown in detail in FIG. 4(g). At this position, the pad encounters a further drive system comprising drive belt 150 and drive cylinders 152 and 154. As shown in FIG. 4(g), drive cylinder 152 is tilted such that its axis makes approximately a 45° angle to the horizontal. At station G, cylinder 152 forces the rear pad portion 54 against angled leg 160 of support member 162. As can be seen, a rounded portion 164 is formed on the angled member 162 and allows a smooth, rounded inner fold at 166 to be provided.

Figure 4H:
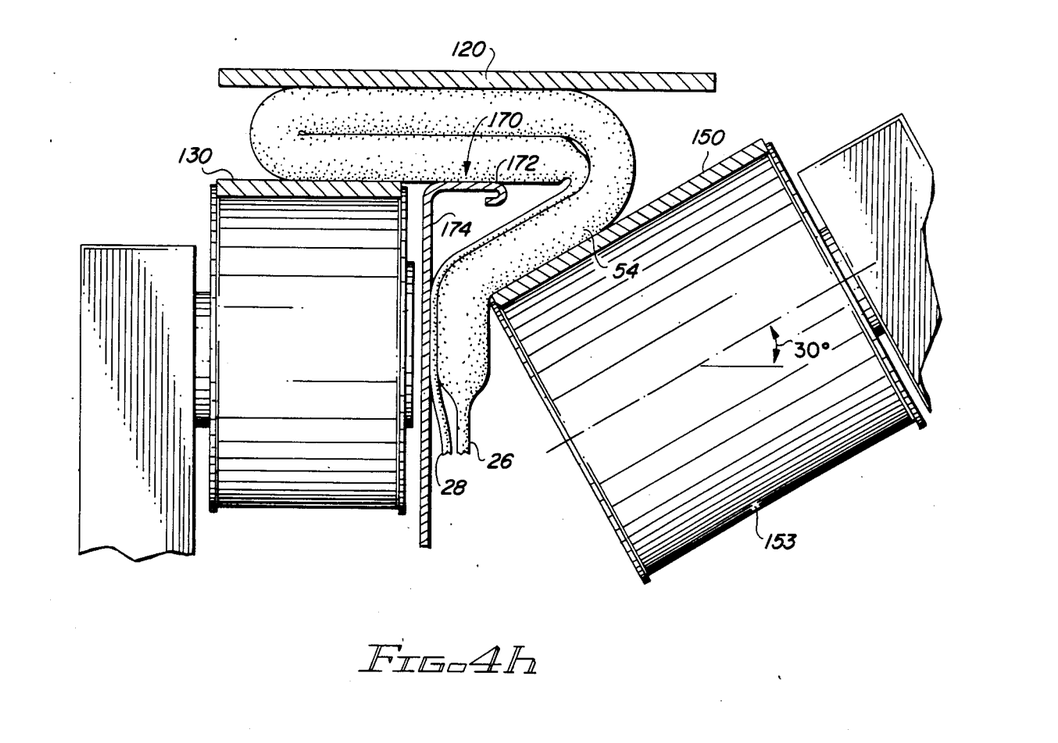
Figure 4I:
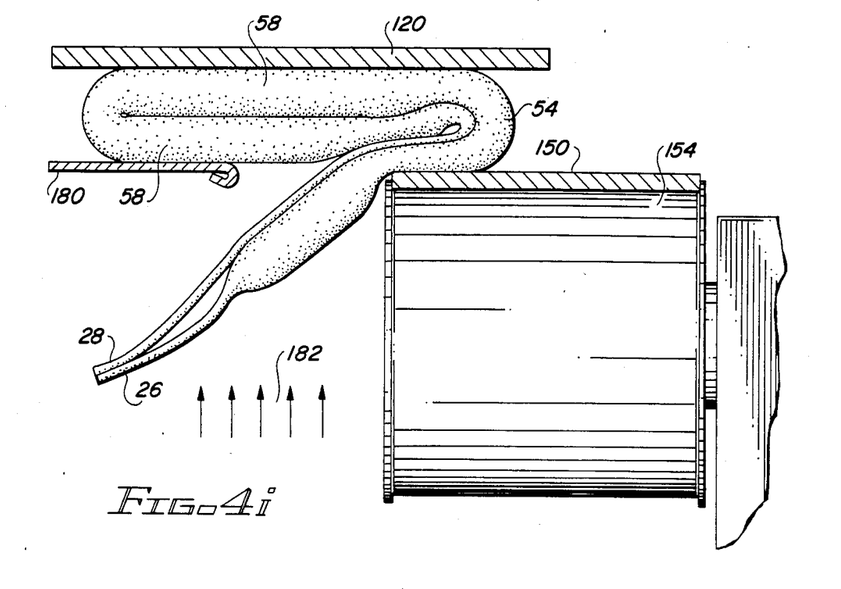

After this operation is performed, pad 10 is advanced to the next station, indicated by reference letter H and shown in more detail in FIG. 4(h). At this position, another drive cylinder 153 is encountered which is tilted at an angle of approximately 30° to the horizontal. Also, shaped guide member 170 is provided adjacent the belt 150 comprising horizontal portion 172 and vertical portion 174. During this operation, drive belt 150 applies a diverting force on rear tail portion 54 to further develop the continuous soft folds of the pad. After the partial folding in station H, pad 10 is advanced to the next station, indicated by reference I and shown in more detail in FIG. 4(i). At this position, front portion 58 of pad 10 is supported by member 180 and drive belt 150 compresses the right-hand portion (as viewed from the plane of the paper) of the now-formed double-folded pad as illustrated. In addition, a blast of air, represented by arrows 182, is applied to the pad 10 as shown to force the unsupported portion of pad 10 toward support member 180.

Figure 4J:
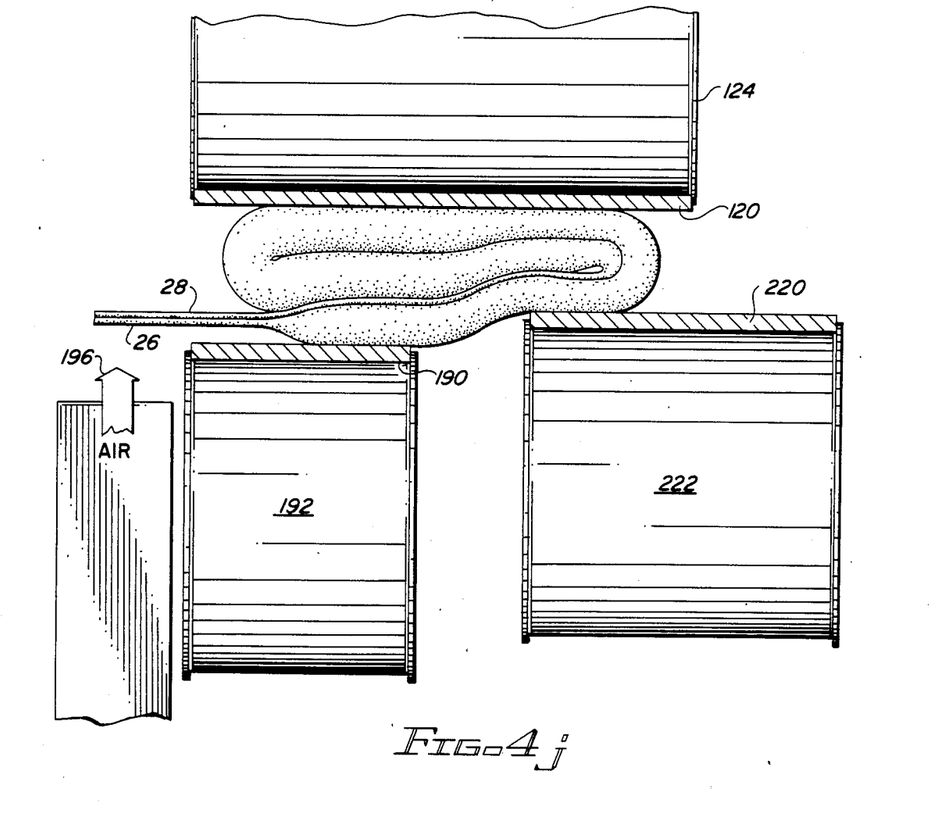

At the next operating station, indicated by reference letter J and shown in detail in FIG. 4(j), additional drive belts 190 on drive cylinders 192 and 194 and 220 on a pair of drive cylinders (cylinder 222 is shown) are encountered. As shown in FIG. 4(j), as the pad 10 continues its advance, bottom fold is supported by the belts 190 and 220. In addition, a blast of air, represented by the arrow 196, is applied to the adjacent tail portions 26 and 28 as illustrated. Leaving station J, the pad follows along on belts 190, 220, passing from under belt 120 to under belt 216 at station K with upper belt 200 added at station L. In particular, drive belt 200 runs about drive cylinders 202 and 204 and a series of drive cylinders 206, 208, 210, 212, 214 and 215 guide drive belt 216.

Figure 4K:
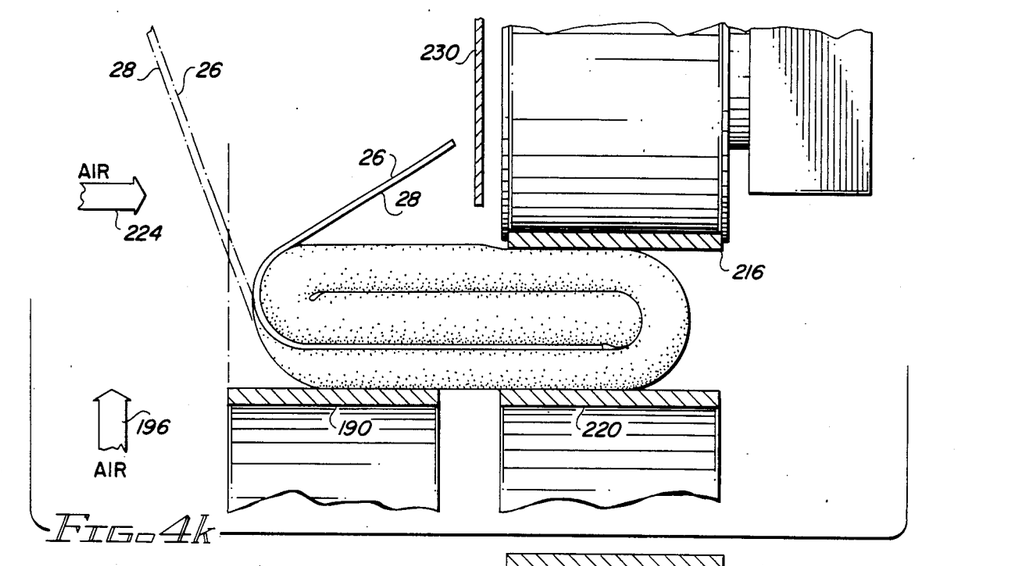

At station K, shown in more detail in FIG. 4(k), the pad 10 is positioned as shown and supported by belts 190, 220 and a portion of belt 216 which acts to compress pad 10 at the contact area. At this point in the operation, a blast of air, represented by the arrow 196, in conjunction with another blast of air, represented by the arrow 224, the latter blast of air being in a substantially horizontal direction, forces the tail portions (as shown in phantom) toward barrier plate 230 as shown in solid lines.

Figure 4L:
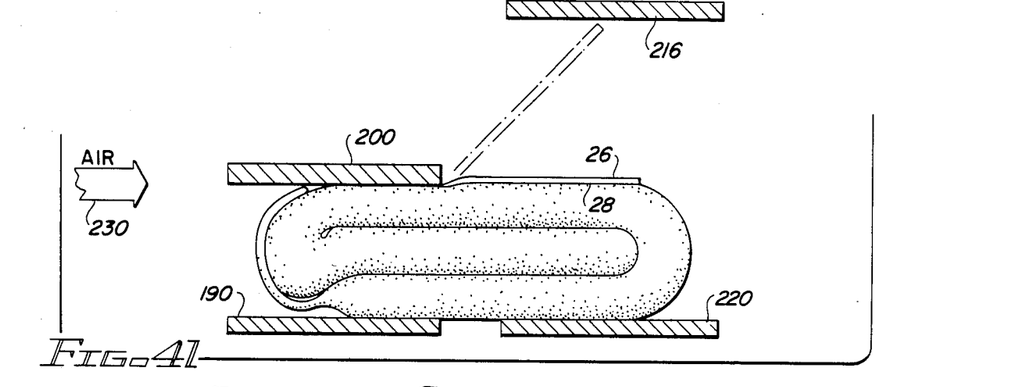

Pad 10 is then advanced to the next station indicated by reference letter L and shown in more detail in FIG. 4(l). In particular, at this point in the operation pad 10 is supported by belts 190 and 220 and compressed and driven by belt 200. Further, belt 200 acts to force the tail portions 26 and 28 down on one end of the pad as shown in the solid lines. The guide roller 215 directs the belt 216 upward and temporarily away from the pad so that a blast of air, indicated by the arrows 230 may act to drive the ends of the tail portions 26 and 28 down on top of the pad in the position under the belt 216.

Although the invention has been disclosed as employing blasts of air at strategic points in the folding process to direct portions of the pad into particular positions, it will be understood mechanical folding bars may be used instead of the blasts of air or in combination with some of them without departing from the scope of the invention.

Figure 4M:
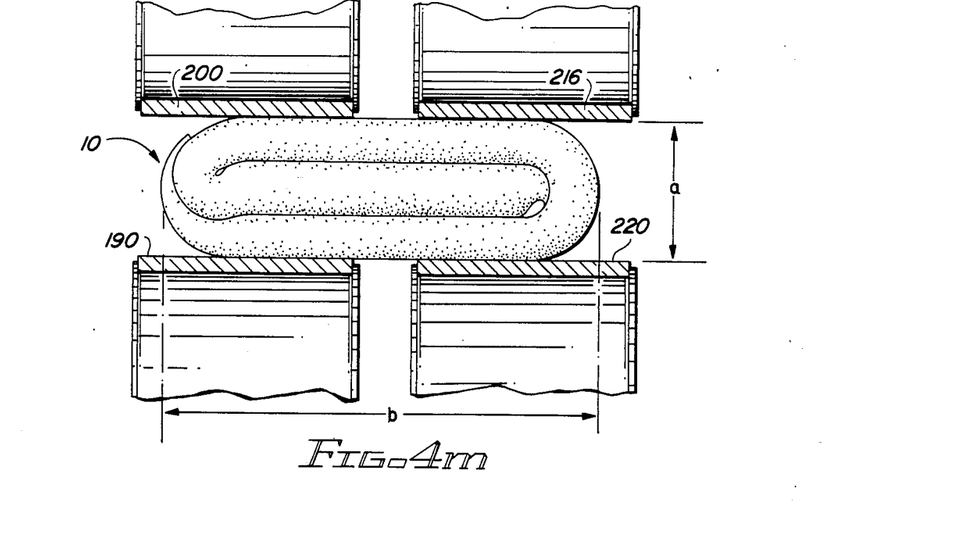

At the final station prior to the completely folded pad leaving the apparatus, indicated by reference letter M and shown in more detail in FIG. 4(m), the pad 10 is engaged by belts 190, 200, 216 and 220 to finally compress the pad into a compact pad having a volume approximately 40% less than the two layer pad shown in FIG. 2. FIGS. 4(l) and 4(m), also FIG. 3, show the three-fold pad which has been formed as described.

A typical size of the folded pad 10 existing from the apparatus 50 is $\frac{7}{8}$ inch thick (reference letter a), $3\frac{1}{2}$ inches long (reference letter b) and three inches wide (reference letter c).

Also shown in the FIG. 3 are the varous drive belts, cylinders and gears utilized to synchronize the drive system 50. The first series of drive means, indicated by reference numeral 250, comprises drive belts 252, 254 and 256 and drive cylinders 258, 260, 262 and 264. Associated with these drive cylinders is a plurality of drive gears 266, 268, 270, 272, and 274, each of the drive cylinders and gears rotating in the direction as shown. The output shaft of the gear 268 is coupled to drive cylinder 70 in the direction of the arrow, the output of gears 270 and 272 being coupled to drive cylinder 64 in the direction of the arrow. The shaft of gear 274 serves to drive associated cylinder 76 in the direction of its arrow, and the shaft of drive cylinder 260 is utilized to drive cylinder 114 in the direction shown.

The second set of drive means, indicated by reference numeral 280, comprises drive cylinders 282, 284, 286 and 288 and drive belt 289 with shafts as indicated. The common shaft of drive cylinders 282, 286 drives cylinder 134 in the direction of the arrow and the common shaft of drive cylinders 284, 288 drives conveyor belt cylinder 154 in the direction of the arrow. The final drive belt means, indicated by reference numeral 290, comprises drive cylinders 292, 294 and 296, drive gears 298, 300 and drive belts 302 and 304, drive belt 304 being common to drive cylinder 284 of drive means 280.

As can be seen, the shaft from drive cylinder 292 drives cylinder 124 in the direction of the arrow, the shaft from gear 298 driving cylinders 204 and 212 in the direction of the arrows, and the output from gear 300 driving cylinders 194 and 224 in the direction of the arrows.

As indicated in FIG. 3, driving force from a motor (not shown) is input via belt 252, passed through the first drive assembly 250 while being split off through the various drive gears 274, 272, 270, 268 and 266 in succession, directed via belt 256 to the second drive assembly 280 while being coupled thereat to intermediate drive shafts coupled to intermediate conveyor belt drive cylinders, and thereafter directed via belt 304 to the output drive assembly 290 comprising the gears 298, 300, take-off belt 302 and final drive pulley 292. By virtue of this arrangement, all of the various steps involved in performing the complex conveying and folding process of the present invention are performed in proper synchronism as each pad 10 proceeds from station to station along the line of the folding apparatus.

Although there have been described above specific arrangements of a pad folding apparatus and methods of operation in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A method for folding an obstetrical pad having a central body portion and first and second end portions at opposite ends of the central body portion, the two end portions having corresponding tail portions extending therefrom, respectively, comprising the steps of:
   delivering an unfolded pad to the input of a series of drive means;
   accepting said unfolded pad and driving said pad through first and second sequences of operating stations;
   folding the first end portion of said pad transversely as it passes through said first sequence of operating stations to position approximately one-third of the pad in substantially parallel juxtaposition along the central body portion of the pad;
   folding the second end portion of said pad transversely around the end of said first end portion and the tail portion extending therefrom as the pad passes through the second sequence of operating stations to position approximately one-third of the pad at said second end portion in substantially parallel juxtaposition with the folded first end portion and central body portion, wherein the second end portion overlaps said first end portion and associated tail portion;
   leading a tail portion from said first end portion outwardly between the overlapped end portions to the exterior of the folded pad; and
   compressing the folded pad in preparation for packaging to provide a compressed folded pad having three pad layers and two transverse folds with both tail portions accessible from outside the folded pad.

2. The method of claim 1 wherein each of said layers comprises approximately one-third of the pad.

3. The method of claim 1 further including the steps of applying blasts of air to initiate each of the folding steps.

4. The method of claim 3 further including the step of deflecting the air flow by means of deflection plates located at stations following the stations where the blasts of air for initiating the folding steps are applied.

5. The method of any one of claims 1, 3 and 4 further including the step of applying a folding belt maintained at a selected angle to increase the degree of folding as the pad progresses through the sequence of operating stations.

6. The method of claim 5 further including the step of continuously increasing the angle of said folding belt in the direction of motion of the pad to progressively increase the degree of folding of the pad.

7. The method of claim 1 further including the step of directing the tail portions into adjacent juxtaposition with each other during the step of folding said second end portion of said pad in said second sequence of operating stations.

8. The method of claim 7 further including the steps of applying blasts of air to selectively direct the tail portions into adjacent juxtaposition with each other.

9. The method of claim 1 further including the step of utilizing a series of conveyor belts for driving the pad through the sequences of operating stations.

10. The method of claim 9 further including the step of driving all of said conveyor belts from a common power source for operation in synchronism.

11. The method of claim 9 further including the step of positioning at least a pair of the conveyor belts opposite each other for propelling the pad between them.

12. The method of claim 11 further including the step of directing the upper belt of said pair away from contact with the pad to permit movement of the tail portions of the pad into position under said upper belt.

13. The method of claim 12 further including the step of using an additional belt on the upper side of the pad to hold the pad in position against a lower belt while the upper belt of said pair is directed away from contact with the pad.

14. The method of claim 1 further including the steps of driving the first and second sequence of operating stations through a power transfer mechanism from a common power source by transferring power from the first sequence to the second sequence while transferring a portion of the power to the first sequence of operating stations.

15. Apparatus for folding an obstetrical pad having a central body portion and first and second end portions at opposite ends of the central body portion, the two end portions having corresponding tail portions extending therefrom, respectively, the apparatus comprising:
   a conveyor belt drive means for receiving an unfolded pad and delivering it in succession to first and second sequences of operating stations;
   means for folding the first end portion of said pad transversely as it passes through the first sequence of operating stations to position approximately one-third of the pad in substantially parallel juxtaposition along the central body portion of the pad;
   means for folding the second end portion of said pad transversely around the end of said first end portion and the tail portion extending therefrom as the pad passes through the second sequence of operating stations to position approximately one-third of the pad at said second end portion in substantially parallel juxtaposition with the remaining portions of the pad in overlapping relationship with the first end portion;

means for directing the tail portion of said first end portion along said second end portion and the tail portion attached thereto; and means for folding the tail portions side by side with each other and along adjacent portions of the folded pad.

16. Apparatus of claim 15 including means for directing the tail portions of the pad into generally parallel alignment with each other.

17. Apparatus of claim 16 further including means for directing the aligned tail portions into folded juxtaposition along an outer surface of the folded pad.

18. Apparatus of claim 17 wherein said tail portion directing means comprises means for applying blasts of air to direct the tail portions into the folded juxtaposition with the pad.

19. Apparatus of claim 18 wherein the tail portion directing means further comprises a pair of conveyor belts extending along the upper surface of the folded pad on opposite sides of the longitudinal centerline thereof, one of said conveyor belts being mounted over an idler pulley which is displaced from the position of the pad so that the belt is temporarily lifted away from the pad in order to permit the tail portions to be moved into position under said one belt.

* * * * *